US006811774B2

(12) United States Patent
Haddada et al.

(10) Patent No.: US 6,811,774 B2
(45) Date of Patent: Nov. 2, 2004

(54) DEFECTIVE RECOMBINANT ADENOVIRUSES EXPRESSING CYTOKINES FOR ANTITUMOR TREATMENT

(75) Inventors: Hedi Mohamed Haddada, Alfortville (FR); Thierry Ragot, Meudon (FR); Michel Perricaudet, Ecrignolles (FR)

(73) Assignees: Centre National de la Recherche Scientifique, Paris (FR); Institut Gustave Roussy, Villejuif Cedex (FR)

(*) Notice: Subject to any disclaimer, the term of this patent is extended or adjusted under 35 U.S.C. 154(b) by 0 days.

(21) Appl. No.: 09/204,427

(22) Filed: Dec. 3, 1998

(65) Prior Publication Data

US 2002/0031499 A1 Mar. 14, 2002

Related U.S. Application Data

(63) Continuation of application No. 08/619,157, filed on Mar. 21, 1996, now abandoned, which is a continuation of application No. 08/469,773, filed on Jun. 6, 1995, now abandoned, which is a continuation of application No. 08/150,011, filed as application No. PCT/FR93/00264 on Mar. 16, 1993, now abandoned.

(30) Foreign Application Priority Data

Mar. 16, 1992 (FR) ............................................. 92 03120

(51) Int. Cl.[7] .......................... A61K 35/00; A61K 48/00
(52) U.S. Cl. .................. 424/93.2; 424/93.1; 424/93.21; 514/44
(58) Field of Search .............................. 424/93.1, 93.2, 424/93.21; 514/44; 435/320.1; 536/23.1

(56) References Cited

U.S. PATENT DOCUMENTS 5,662,896 A * 9/1997 Barber et al. ............... 424/93.2
6,013,638 A * 1/2000 Crystal et al. ................ 514/44
6,297,219 B1 * 10/2001 Nabel et al. .................. 514/44

FOREIGN PATENT DOCUMENTS

| EP | 0185573 | | 6/1986 |
| WO | WO 88/00971 | | 2/1988 |
| WO | 2 688 514 | * | 3/1992 |
| WO | WO 93/19191 | * | 9/1993 |

OTHER PUBLICATIONS

Lebovitz et al., Parvovirus H–1 Expression: Mapping of the Abundant Cytoplasmic Transcripts and Identification of Promoter Sites and Overlapping Transcription Units, May 1986, Journal of Virology, vol. 58 No. 2 pp. 271–280.*

Gu et al., Parvovirus H–1 Promoter Reguires the trans–Activation Region (tar), and SP1 site, and a TATA Box for Full Activity, 1992, Virology, 187 pp. 10–17.*

Addison, C, et al., "Intranumoral injection of an adenovirus expressing intericulum in 2 induces regression and immunity in a marine breast cancer model", *Proc. Natl. Acad. Sci. USA*, 92:8522–8526 (Aug. 1995).

Schmit.Wolf, G. et al., "Cytokines and clinical gene therapy", *Eur. J. Immunol.*, 25:1137–1140 (1995).

Clark, I. et al., "Roles of TNF in malaria and other parasitic infections", *Imunnology Series*, 56:365–407 (1992) Medicine Accession No. 92199019 (Abstract only).

Ovington, K. et al., "Cytokines and immunological control of Elmeria spp.", *International Journal for Parasitology*, 25(11):1331–51 (Nov. 1995) Medline Accession No. 96229273 (Abstract only).

Brunda, M. J., "Interleukin–12", *Journal of Leukocyte Biology*, 56(2):280–288 (Feb. 1994) Medline Accession No. 94132739 (Abstract only).

Utsunomiya, T. et al., "A relationship between the generation of burn–associated type 2 T cells and their antagonistic cells in thermally injured mice", *Burns*, 23(4):281–287 (Jun. 1997) Medline Accession No. 97391891 (Abstract only).

Gluzman et al., Euhágste Vinl Vectors, pp. 187–192 (1982).

Gratham, F.L. et al., *J. Gen. Virol.*, 36:59–72 (1977).

Quantin et al., "Adenovirus as an Expression Vector in uscle Cells Application to Dystrophin", *Collogue Inserm*, (Human Gene Transfer, International Workshop, Paris, France), 219:271–272 (Apr. 11, 1991).

Rosenfeld et al., "Adenovirus–mediated Transfer of a Recombinant Alpha–alntitrypsin Gene to the Lung Epithelium in Vivo", *Science*, 252(5004):431–434 (Apr. 19, 1991).

Russell, S.J., "Lymphokine Gene Therapy for Cancer", *Immunology Today*, 11(6):196–200 (Jun. 1990).

Stratford–Perricaudet, et al., "Gene Transfer into Animals: The Promise of Adenovirus", *Collogue Inserm*, (Human Gene Transfer, International Workshop, Paris, France), 219:51–61 (Apr. 11, 1991).

Venkatesh et al., "Selective Inductiono fToxicity to Human Cells Expressing Human Immunodeficiency Virus Type I Tat by a Conditionally Cytotoxic Adenovirus Vector", *Proceedins of the National Academy of Sciences of USA*, 87(22):8746–8750 (Nov. 1990).

Winkinson, GWG et al., "Constitutive and Enhanced Expression from the CMV Major IE Promoter in a Defective Adenovirus Vector", *Nucleic Acids Research*, 20(9):2233–2239 (May 11, 1992).

(List continued on next page.)

*Primary Examiner*—Michael C. Wilson
(74) *Attorney, Agent, or Firm*—Merchant & Gould P.C.

(57) ABSTRACT

A recombinant nucleic acid used for the production of a defective adenovirus containing an inserted sequence coding for a cytokine under the control of a promoter in the genomic sequence of the recombinant adenovirus. This recombinant adenovirus is useful in the preparation of anti-tumoral drugs which can be directly injected into the tumor of the host.

1 Claim, 1 Drawing Sheet

OTHER PUBLICATIONS

Graham, F., "Undercurrents: Adenovirus as expression vectors and recombinant vaccines," *Tibtech*, 8:85–87 (Apr. 1990).

Rosenberg, S. et al., "A Progress Report on the Treatment of 157 Patients with Advanced Cancer Using Lymphokine–Activated Killer Cells and Interleukin–2 or High–Dose Interleukin–2 Alone," *The New England Journal of Medicine*, 316(15):889–896 (Apr. 9, 1987).

Singh, S. et al., "Up–Regulation by Granulocyte–Macrophage Colony–Stimulating Factor (GM–CSF) of Induction of Lymphokine (IL–2)–Activated Killer (LAK) Cells by Human Blood Monocytes," *Int. J. Cancer*, 44:170–176 (1989).

Serfling, E. et al.; "Metal–dependent SV40 viruses containing inducible enhancers from the upstream region of metallothionein genes", *IRL Press Limited, Oxford, England*, pp. 3851–3859.

Ponta, H. et al., "Hormonal response region in the mouse mammary tumor virus long terminal repeat can be dissociated from the proviral promoter and has enhancer properties," pp. 1020–1024.

Israel, D. et al., "Highly inducible expression from vectors containing multiple GRE's in CHO cells overexpressing the glucocorticoid receptor," *Nucleic Acids Res.*, 17(12):4589–4604 (Jun. 26, 1989) (Abstract only).

Wilkinson, G. et al., "Constitutive and enhanced expression from the CMV major IE promoter in a defective adenovirus vector", *Nucleic Acids Research*, 20(9):2233–2239 (1992).

Colicos, M. et al., "Construction of a recombinant adenovirus containing the denV gene from bacteriophase T4 which can partially restore the DNA repair deficiency in xeroderma pigmentosum fibroblasts", *Carcinogenesis*, 12(2):249–255 (Feb. 1991) (Abstract only).

Squiban, P., "France. Transgene Announces Progress in Cancer Clinical Development Programs", *TCLine News*, May 14, 2003 (3 pages).

Squiban, P., "Transgene Presents Positive Phase I/II Data on its Adeno–Interferon Gamma Product in Cutaneous Lymphoma at the American Society of Gene Therapy Meeting", *TCLine News*, Jun. 11, 2003. (2 pages).

Slos, P. et al., "Immunotherapy of established tumors in mice by intratumoral injection of an adenovirus vector harboring the human IL–2 cDNA: Induction of CD8+ T–cell immunity and NK activity", *Cancer Gene Therapy*, vol. 8, No. 5, pp. 321–332 (2001).

Ahmed, C., et al. "In Vivo Tumor Suppression by Adenovirus–Mediated Interferon α2b Gene Delivery", *Human Gene Therapy*, vol. 10, pp. 77–84 (Jan. 1, 1999).

Fujii, S., et al. "Activated Dendritic Cells From Bone Marrow Cells of Mice Receiving Cytokine–Expressing Tumor Cells Are Associated With the Enhanced Survival of Mice Bearing Syngeneic Tumors", *Blood*, vol. 93, No. 12, pp. 4328–4335 (Jun. 15, 1999).

Miller et al., Targeted vectors for gene therapy, 1995, FASEB, vol. 9, pp. 190–199.*

Deonarain, Ligand–targeted receptor–mediated vectors for gene delivery, 1998, Exp. Opin. Ther. Patents, vol. 8, pp. 53–69.*

Verma et al., Gene therapy–promises, problems and prospects, 1997, Nature, vol. 389, pp. 239–242.*

Crystal, Transfer of genes to humans: Early lessons and obstacles to success, 1995, Science, vol. 270, pp. 404–410.*

Bramson et al., *Direct Intraturmoral Injection of an Adenovirus Expressing Interleukin–12 Induces Regression and Long–Lasting Immunity That is Associated with Highly Localized Expression of Interleukin–12*, Human Gene Therapy 7:1995–2002 (1996).

Cordier et al., *Complete recovery of mice from a pre–established tumor by direct intratumoral delivery of an adenovirus vector harboring the murine IL–2 gene*, Gene Therapy, 2:16–21 (1996).

Gambotto et al., *Induction of antitumor immunity by direct intratumoral injection of a recombinant adenovirus vector expressing interleukin–12*, Cancer Gene Therapy, vol. 6, No. 1, pp. 45–53 (1999).

Huang et al., *Gene therapy for hepatocellular carcinoma: long–term remission of primary and metastatic tumors in mice by interleukin–2 gene therapy in vivo*, Gene Therapy, 3(11):980–7 (1996).

Leroy et al., *Cancer immunotherapy by direct in vivo transfer of immunomodulatory genes*, Res. Immunol., 149:681–684 (1998).

Kendra et al., *Phase I Trial of Immunotherapy with Adenovirus–Interferon–γ (TG1041) in Patients with Malignant Melanoma*.

Stewart et al., *Adenovector–mediated gene delivery of interleukin–2 in metastatic breast cancer and melanoma: results of a phase I clinical trial*, Gene Therapy, 6:350–363 (1999).

Toloza et al., *Transduction of murine and human tumors using recombinant adenovirus vectors*, Ann. Surg. Oncol., 4(1):70–9, (1997).

Tursz et al., *Phase I study of a recombinant adenovirus–mediated gene transfer in lung cancer patients*, J. Natl. Cancer Inst., 88(24):1857–63 (1996).

Zhang et al., *Treatment of a human breast cancer xenograft with an adenovirus vector containing an interferon gene results in rapid regression due to viral oncolysis and gene therapy*, Proc. Natl. Acad. Sci., 93(9):4513–8 (1996).

* cited by examiner

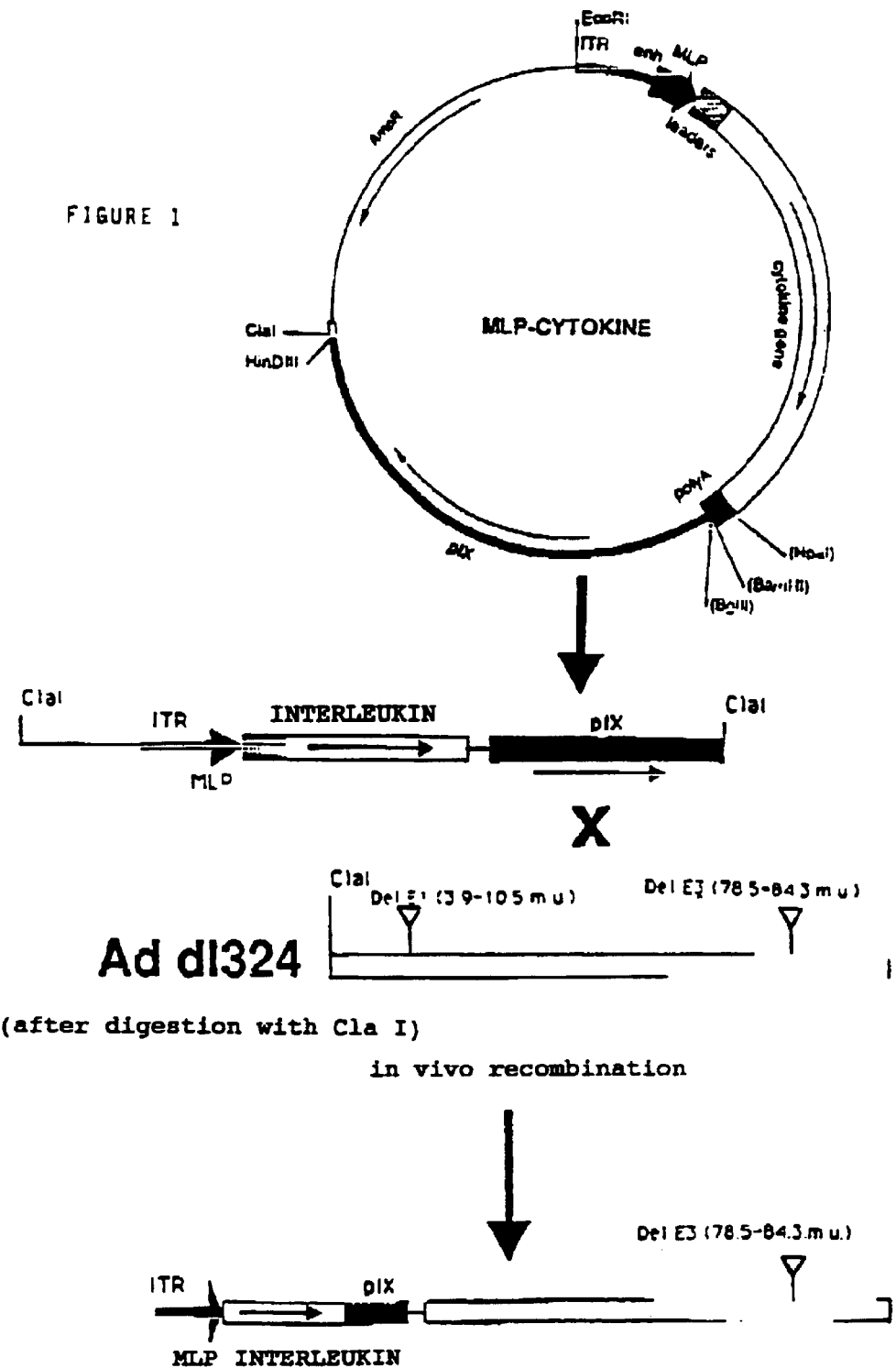

DEFECTIVE RECOMBINANT ADENOVIRUSES EXPRESSING CYTOKINES FOR ANTITUMOR TREATMENT

This application is a continuation of Ser. No. 08/619,157 filed Mar. 21, 1996, abandoned, which is a continuation of Ser. No. 08/469,773, filed Jun. 6, 1995, abandoned which is a continuation of Ser. No. 08/150,011, filed Jan. 13, 1994, abandoned, which was the national phase of PCT/FR93/00264, filed Mar. 16, 1993 as WO/9319191.

BACKGROUND OF THE INVENTION

1. Field of the Invention

Cytokines are molecules (hormones) produced by cells following an antigenic stimulation or an activation by other factors. The first cytokine which will has been produced is interleukin-1 (Il-1). It permits activation of the T cells which, in turn, start producing a whole battery of lymphokines, some of which are essential for the activation of the immune system and the defenses against viral or parasitic infections.

2. Description of Related Art

For some years, cytokines have been used in anticancer immunotherapy. Nevertheless, when they are administered systemically, a number of problems arise. Il-2, for example, produces quite substantial side effects, it is rapidly metabolized, so that high doses have to be administered repeatedly.

Better administration routes which would increase their efficacy while decreasing their adverse effects are hence being sought.

SUMMARY FOR THE INVENTION

The subject of the invention is hence defective recombinant adenoviruses expressing one or more cytokines, as well as the use of these recombinant adenoviruses for making up pharmaceutical compositions, in particular antitumor compositions, more especially compositions which can be injected directly into solid tumors of the host.

The subject of the present invention is defective recombinant adenoviruses, characterized in that they contain a defective, non-replicable adenovirus genome into which one or more nucleic acid sequences coding for one more cytokines, in particular lymphokines, are inserted under the control of one or more promoters capable of being recognised by the polymerases of human cells, more especially of human tumor cells or of cells infiltrating these tumors.

BRIEF DESCRIPTION OF THE DRAWINGS

FIG. 1 shows diagrammatically a construct of a defective recombinant adenoviral vector employing an insertion sequence coding for an interleukin (IL-2, IL-4 and the like).In this figure, "leaders" corresponds to a tripartite leader, "Del" corresponds to a "deletion" and Ad dl 324 corresponds to an adenovirus provided with the above-mention "deletions."

DETAILED DESCRIPTION OF THE PREFERRED EMBODIMENTS OF THE INVENTION

The invention relates more especially to recombinant nucleic acids capable of being used for the production of such defective recombinant adenoviruses.

Such a recombinant nucleic acid is characterized in that it contains, on the one hand a genomic sequence of an adenovirus which is defective in that it lacks the sequences needed for its replication, but which nevertheless contains those sequences which, in this genome, are the carrier of the genetic information needed for the corresponding adenovirus to enter the cells which the latter is capable of infecting, as well as the set of essential sequences needed for encapsidation of this adenovirus, and on the other hand an insert containing a nucleic acid sequence coding for a cytokine, this insert being under the control of a promoter present in or previously inserted into the abovementioned genomic sequence.

Adenoviruses, in particular type 2 or 5 adenoviruses capable of infecting humans (or human adenoviruses), or alternatively serotype 4 and 7 adenoviruses, represent especially preferred vectors in the context of the present invention, on account, in particular, of the large size of the foreign DNA fragment which it is possible to insert into the genome of these viruses.

Advantageously the abovementioned nucleic acid insertion sequence(s), coding for one or more predetermined cytokines, are contained in a defective adenovirus genome lacking the essential nucleotide sequences needed for replication of these adenoviruses, and more especially the transactivators E1A and E1B and, where appropriate, the E3 region of the adenovirus, or alternatively its E1 and E3 regions.

In other words, the invention turns to good account the capacity of these defective recombinant adenoviruses to allow the insertion sequence they contain to be expressed in the cells they invade even when, on account of their defective character, they do not multiply therein. In other words, the objective of the invention is to cause cytokines to be secreted actually within the cells of the tumor to be treated (tumor cells themselves and cells, in particular lymphocytes, which infiltrate these tumors) when these cells have been infected with these defective adenoviruses, especially when the latter are injected directly into the tumor. The cytokines produced will thus activate first and foremost, in situ, the cytotoxic cells infiltrating the tumor and those present in proximity to the tumor.

Regarding the sequence for insertion into the defective recombinant adenovirus genome, this may be chosen from all those which express a cytokine capable of exerting either a direct antitumor effect, or an activating effect on immunocompetent cells of the body, or both together.

Among these cytokines, the following may be mentioned as examples: IL-1, IL-2, IL-3, IL-4, IL-5, IL-6, α interferon, γ interferon, tumor necrosis factor alpha (TNFα) ([same term in French]).

The same recombinant adenoviruses may also be used in the case of certain diseases in which there is an immune deficiency and in the case of certain parasitic or viral diseases, especially γ, α interferon and/or GM-CSF), in particular by administration systemically or via cells, preferably human cells, taken in a state that allows them to be injected into humans, these cells having previously been infected with a recombinant defective adenovirus according to the invention.

The properties of some of these cytokines are recalled below.

Interleukin-1 (IL-1):

This is produced essentially by activated macrophages and monocytes. Its molecular weight is approximately 17 kilodaltons. It displays several activities, including:

a) a chemoattractive action on polymorphonuclear cells and macrophages (1, 2), b) an increase in the cytotoxic activity of spontaneous cytotoxic (natural killer or Nk cells),
c) an induction of fever following an infection,
d) most especially, the activation of T cells for the production of other factors.

Interleukin-2 (IL-2), Interleukin-4 (IL-4) and Interleukin-5 (IL-5):

These are produced by activated T lymphocytes. The action of these cytokines is restricted to cells of the immune system, they cause their multiplication and their activation: IL-2 and IL-4 have been tested in antitumor immunotherapy in mice and in man. In mice, they act synergistically and cause tumor regression.

Interleukin-6 (IL-6)

This is produced by many cell types including T lymphocytes, macrophages, fibroblasts, etc. It induces the final differentiation of B lymphocytes, which become antibody producers.

Tumor Necrosis Factor α (TNFα) ([Same Term in French]):

This is a factor produced by macrophages. It has a dual action: a direct action on tumor cells causing their lysis and an activation of the immune system.

The use of TNFα in man must be carried out cautiously since a large number of cells possess the receptor for it: which accounts for the importance of inducing its secretion only locally, actually within the tumor, to limit its adverse effects on the other cells of the host.

Interleukin-3-(IL-3), Interleukin-7 (IL-7) and Colony Stimulating Factor (CSF).

These are hematopoietic growth factors. They are produced essentially by lymphocytes, monocytes and macrophages. They act at different levels of hematopoiesis, that is to say of the different stages of differentiation of marrow cells to blood cells. In addition, CSF exerts very substantial effects on the body's primary defenses as regards the bacterial defenses, luring the macrophages to the sites of infection and increasing their capacity for phagocytosis.

In combination with IL-2 and IL-4, GM-CSF proves to be an important antitumor factor.

γ Interferon (IFN-γ)

This is a factor produced by activated T cells; it is endowed with antiviral properties; it inhibits the multiplication of viruses and parasites and causes the lysis of infected cells and some tumor cells.

α Interferon (IFN-α)

Produced by T cells and monocytes, this displays an antiviral and lyric effect on infected cells. IFN-α has been used in immunotherapy against some types of cancer, including mesothelium [sic].

Naturally, the invention is not limited, as regards the choice of insertion sequences which can be used in adenoviruses according to the invention, to those sequences which have been identified above. Nevertheless, the latter are illustrative of the palette of possibilities which are afforded to the therapist, who is responsible for making the choice of the most suitable defective recombinant adenovirus to be used in the light of the nature of the tumors to be combated.

The invention also relates to pharmaceutical compositions comprising one or more recombinant vectors as described above, in combination with a pharmaceutically acceptable vehicle, especially sterile, isotonic compositions which can be injected directly into the tumors to be treated, or dry, in particular lyophilized, compositions which, by the addition of sterilized water or of physiological saline as the case may be, enable solutions which can be injected directly into the tumors to be made up or reconstituted.

Direct injection of non-replicable, modified adenoviruses into the tumor affords the advantage, on the one hand of avoiding diffusion of the recombinant adenoviruses in the general circulation, with the consequent side effects liable to be exerted by the cytokines expressed in places other than on the sites where the manifestation of their action is sought, in this instance the tumor cells themselves or the cells, in particular lymphocytes, which infiltrate them or which are present in their immediate proximity. Preferably, the injection is carried out at the very least in at least one site of the primary tumor.

Neither is the invention limited to administration of the recombinant adenoviruses containing the sequences coding for the cytokines of the kind in question directly in the tumors. Any other administration route permitting access of these recombinant adenoviruses to the tumor to be treated may be envisaged. In particular, use may be made of cells which are compatible with the host, for example human fibroblasts, preferably ones previously removed from the host him- or herself.

The invention also relates to cell cultures, for example cultured fibroblasts previously infected with recombinant nucleic acids, more especially the defective adenoviruses defined above. These infected cells, where appropriate attenuated or rendered immunologically inert, for example by irradiation, contribute to the eradication of installed tumors when they are injected systemically. This injection may be envisaged either alone, or in addition to injection directly into the tumor.

The subject of the invention is also a method for obtaining the recombinant adenoviruses described above, which comprises, after the actual step of construction of a vector by introduction of one or more insertion nucleic acid(s) into the genome of the initial defective adenovirus, a step of transformation of transformable cell lines of higher eukaryotes (in particular of human or animal origin) themselves containing a separate nucleotide sequence capable of complementing the portion(s) lacking in the genome of the defective adenovirus and without which replication of the latter is prevented, said separate sequence preferably being incorporated in the genome of the cells of said cell line.

As a preferred example of such cell lines, there may be mentioned line 293, a human embryonic kidney line which contains, integrated in its genome, the first eleven percent of the left-hand end of the genome of a type 5 adenovirus (Ad5). This fraction can then complement defective recombinant viruses which carry deletions of this region. Such a production method is described, more especially, in European Patent Application No. 0,185,573 of Nov. 20, 1985.

After transformation of these cell lines, the defective adenoviruses thus multiplied and produced are recovered from the culture medium of the cells of these lines and purified.

Further details of the present invention will be given in the description which follows of the possibilities of construction of a recombinant vector adenovirus containing at least one sequence coding for a cytokine, especially a lymphokine.

I. Methods

A) Cells and Viruses

Ad-5-transformed human embryonic kidney cell line 293 (Graham et al., 1977) was used for the transfection of DNA as well as for the multiplication and titration of adenovirus (Ad). In effect, cell line 293 complements the functions of the genes for E1A and E1B functions and permits the replication of defective Ad recombinants. For the construction of the recombinant Ad, human Ad5-d1324, carrying deletions in the E1 region (3.9–10.5 m.u.) and E3 region (78.5–84.3 m.u.), was used (Shenk and Williams, 1984). Cell lines 293, Hela [sic] and Vero were maintained in an Eagle minimum essential culture medium with 10% of fetal calf serum.

b) Construction of Plasmids Permitting the Expression of Different Cytokines

The eukaryotic expression vector pMLP10 has been described (Ballay et al., 1985). A derivative of this vector (pMLP18) was constructed by insertion of a sequence containing different single restriction sites downstream of the adenovirus major late promoter. These sites thus permit cloning of the different genes coding for the chosen cytokines under the control of the viral promoter. Downstream of this sequence containing these single restriction sites, the sequence containing the polyadenylation signal of the gene coding for the early antigens of SV40 virus were placed. The BgIII-HindIII fragment of Ad5 is cloned downstream. This 3-Kbp sequence contains the gene coding for protein IX which is necessary for encapsidation of the viral genome exceeding 97% of its normal size, and permits subsequent in vivo recombination. Sequences coding for the genes for the different cytokines are isolated from plasmids obtained from different teams. These sequences, obtained after cleavage by means of different restriction enzymes, are introduced into the multiple cloning site of the expression vector described above (pMLP-18). The different plasmids designated pMLP-cytokine (IL-2, IL-4, and the like), which are used for obtaining the recombinant viruses as described in the following section, are thereby obtained.

c) Transfection of DNA and Isolation of Recombinant Viruses

The Ad-cytokine defective recombinant adenoviruses were obtained by in vivo recombination between the straight fragment of the viral genome previously cleaved with the restriction enzyme Cla I and the homologous sequence existing on the plasmids pMLP-cytokine described above. The mixture of the fragment of the viral genome (2.6 m.u.–100 m.u.), purified after cleavage, and of the plasmid linearized with the restriction enzyme Cla I or Pvu I is transfected into 293 cells using the calcium phosphate precipitation method (Graham and Van der Eb, 1973). Cell plaques showing a cytopathic effect are isolated 10 days later and the virus was amplified in culture. The viral DNA was extracted by the Hirt procedure (Graham et al., 1977) and the recombinant viruses were identified by mapping with restriction enzymes.

d) Expression of the Sequences Coding for an Expressed Cytokine

Hela or Vero cell lines are infected with the defective recombinant viruses obtained. Cells effectively transfected may be characterized essentially by means of detection of the activity of the cytokine released into their culture medium. In the case of IL-I, yields capable of reaching from 1 to 2 $\mu$g of interleukin per $10^6$ cells have been observed.

Cells infected with an Ad-cytokine recombinant secrete variable amounts of the cytokine into the culture medium. Different methods exist for the detection and quantification of the cytokines produced.

1) Quantitative methods:
   ELISA, using specific antibodies
   RIA (radioimmunoassay)
   Western blotting
2) Qualitative methods (or biotests): based on the biological properties of cytokines
   For example:
   IL-2: Test of proliferation of CTL-L2 cells (CTL-L2 cells multiply and are maintained in culture only in the presence of IL-2 in the culture medium)
   IL-3 and GM-CSF: Test of proliferation of TF-1 cells
   IL-4: Test of proliferation of CTL-L2 cells and induction of soluble CD23 with certain cells including lymphocytes.
   INF-$\alpha$: Cytotoxicity test on L92–9 cells.
   Neutralization test: The effect of cytokines may be blocked by incubating the target cells in the presence of cells of specific antibodies.

Some results obtained with the adenovirus vector carrying the IL-2 gene (Ad-IL-2) are described below.

1) Cells infected in vitro with Ad-IL-2 secrete significant amounts of functional IL-2.
2) Direct injection of the vector carrying the IL-2 gene into tumors already established in the animal (the tumor diameter at the time of injection is between 4 and 7 mm) induces stimulation of the immune system which manifests itself in a stabilization of the size of the tumor, and then its regression to the point of complete disappearance in 40% to 50% of cases.

This result may be improved by treating the tumors in an earlier phase of its development or by using different vectors at the same time, for example combination of Ad-IL-2 with Ad-INF and/or Ad-IL-4, Ad-GM-CSF, Ad-IL-3. This combination has to be specified according to the type of tumor.

3) Tumor cells infected in vitro and then injected into syngeneic animals or even immunodeficient animals (Nu/Nu mice) lose their tumorigenic power (at least up to 80% of the animals reject the tumor cells; in other words, the tumor cells no longer proliferate in 80% of immunodeficient animals injected with these cells.
4) Animals which have rejected a first injection of infected tumor cells are highly immunized and are protected against parent (uninfected) tumor cells injected at different times and at different places.

When coinjected with tumor cells infected in vitro, the spleen cells of these immunized animals are, furthermore, capable of transferring the antitumor immunity to recipient animals.

It is self-evident that the descriptions of constructions of recombinant defective adenoviruses envisaged above are in no way limiting in character. Other constructions may be produced, in particular according to the variants also mentioned below as examples.

1) Promoter Exchange

The adenovirus major late promoter may be replaced by other promoters which are ubiquitous but of exogenous origin, such as:
   promoter contained in the LTR (long terminal repeat) of RSV (Rouse sarcoma virus)
   the promoter of the IE gene of CMV (cytomegalovirus)
   the MMTV (mouse mammary tumor virus) or metallothionine inducible promoters.

Similarly, promoters permitting a more specific expression restricted to tumor cells, may be used, such as, for example:
   the promoter of the rep gene of parvovirus HI.

The invention also relates to a recombinant nucleic acid of the abovementioned type, characterized in that the genomic sequence of the adenovirus lacks its 5' end region downstream of the early promoter of the E1A region of the adenovirus, and in that the sequence coding for the cytokine is placed under the control of this early promoter. This recombinant nucleic acid may also be employed in applications mentioned more especially in connection with recombinant DNAs in which the sequence coding for the cytokine is placed under the control of the adenovirus major late promoter.

2) Simultaneous Expression of Several Cytokine Genes 3 types of constructions are described:

the cytokine genes are under the control of two promoters which are either identical or different (MLP and RSV, for example) and are located following one another.

the cytokine genes are under the control of separate promoters cloned into separate regions of the virus.

What is claimed is:

1. A method for treating a tumor in patients in need of such treatment, said method comprising injecting an effective amount of a pharmaceutical composition into said tumor wherein said pharmaceutical composition comprises:

(a) a replication-defective adenoviral vector lacking the E1A, E2B and E3 regions of an adenovirus; and comprising a nucleic acid sequence coding for a cytokine, under the control of an adenovirus late promoter, and wherein said cytokine is interleukin-2; and (b) a pharmaceutically acceptable vehicle, wherein said pharmaceutical composition causes regression of said tumor in at least 40% to 50% of patients.

* * * * *

UNITED STATES PATENT AND TRADEMARK OFFICE
CERTIFICATE OF CORRECTION

PATENT NO.   : 6,811,774 B2
DATED        : November 2, 2004
INVENTOR(S)  : Haddada et al.

It is certified that error appears in the above-identified patent and that said Letters Patent is hereby corrected as shown below:

Column 8,
Line 2, "E2B" should read -- E1B --

Signed and Sealed this

Tenth Day of May, 2005

JON W. DUDAS
*Director of the United States Patent and Trademark Office*